United States Patent [19]

Weisrock et al.

[11] 4,374,929
[45] Feb. 22, 1983

[54] PRODUCTION OF XANTHAN GUM FROM A CHEMICALLY DEFINED MEDIUM INTRODUCTION

[75] Inventors: William P. Weisrock, Broken Arrow, Okla.; Harriet S. Klein, Glen Ellyn, Ill.

[73] Assignee: Standard Oil Company (Indiana), Chicago, Ill.

[21] Appl. No.: 317,372

[22] Filed: Nov. 2, 1981

Related U.S. Application Data

[63] Continuation-in-part of Ser. No. 167,893, Jul. 14, 1980, abandoned.

[51] Int. Cl.³ .................. C12P 19/06; C12R 1/64
[52] U.S. Cl. .................................. 435/104; 435/813; 435/910
[58] Field of Search .................. 435/104, 813, 910

[56] References Cited

U.S. PATENT DOCUMENTS 3,328,262 6/1967 Lindblom et al. .................. 435/104
3,485,719 12/1969 Rogovin .............................. 435/104

FOREIGN PATENT DOCUMENTS 7612448 5/1977 Netherlands .
1512536 1/1978 United Kingdom .
2008138A 5/1979 United Kingdom .

OTHER PUBLICATIONS

Davidson, FEMS Microbiology Letters, vol. 3, pp. 347–349.
Silman et al., Biotechnology and Bioengineering, vol. XIV, pp. 23–31 (1972).
Silman et al., Biotechnology and Bioengineering, vol. XII, pp. 75–83 (1970).

Primary Examiner—Lionel M. Shapiro
Attorney, Agent, or Firm—Stephen R. May; Fred E. Hook

[57] ABSTRACT

A process is described for the continuous manufacture of xanthan gum in which continuous culture is conducted under conditions of nutrient limited growth using relatively inexpensive chemically defined media containing certain vitamins with or without amino acids. The process is directed broadly to use of bacteria of the genus *Xanthomonas* to produce xanthan gum from the aforesaid media.

15 Claims, No Drawings

PRODUCTION OF XANTHAN GUM FROM A CHEMICALLY DEFINED MEDIUM

INTRODUCTION

This is a Continuation-in-Part of application Ser. No. 167,893, filed July 14, 1980, now abandoned.

INTRODUCTION

The process of the present invention relates to a method for the continuous production of high molecular weight heteropolysaccharide polymers by the action of bacteria of the genus *Xanthomonas campestris* on chemically defined media containing certain organic supplements such as vitamins with or without amino acids containing assimilable nitrogen.

BACKGROUND OF THE INVENTION

Earlier work has indicated that heteropolysaccharides produced by the action of Xanthomonas bacteria on carbohydrate media have potential application as film forming agents, as thickeners in edible products, cosmetic preparations, pharmaceutical vehicles, oil field drilling fluids, fracturing liquids, similar compositions, and as emulsifying, stablizing, and sizing agents. Heteropolysaccharides, particularly, xanthan gum, have significant potential as mobility control agents in micellar polymer flooding. Xanthan gum has excellent viscosifying properties at low concentration, is resistant to shear degradation and exhibits only minimal losses in viscosity as a function of temperature, pH, and ionic strength. For these reasons, xanthan gum is an attractive alternative to synthetic polyacrylamides for enhanced oil recovery operations.

Fermentation of the inoculated medium with Xanthomonas organisms for 36-72 hours under aerobic conditions results in the formation of xanthan gum which is separated from other components of the medium by precipitation with acetone or methanol in a known manner. Because of time required to ferment each batch, the low biopolymer content of the fermented medium and the processing required for the recovery and purification of the product, xanthan is relatively expensive.

Other investigators have produced xanthan heteropolysaccharide by means of single stage or multistage "continuous" fermentation. In most instances, *Xanthomonas campestris* was grown in a medium containing dried distillers solubles (DDS) or other complex nutrient as a source of nitrogen and growth factors. There has been no instance of which we are aware, however, that xanthan was produced by continuous fermentation with *Xanthomonas campestris* or any organism of the Xanthomonas genus using a chemically defined medium containing glucose, ammonium chloride, mineral salts, and an organic supplement consisting of vitamins and/or amino acids.

It is well-known that continuous production of xanthan can be hampered by a tendency of the culture (*Xanthomonas campestris*) to change or degenerate after a specific number of turnovers; i.e., the time required to completely replace one volume of broth in the fermentation vessel, or the reciprocal of the dilution rate. Normally, 6 to 9 turnovers are the maximum that can be obtained before degeneration of the culture occurs. Coincident with degeneration, there is a decrease in xanthan viscosity, a loss in volumetric productivity of xanthan, i.e., grams of xanthan produced per liter of broth per hour, and the appearance of variant strains that no longer produce xanthan or else produce a poor quality of xanthan. It has been demonstrated that this phenomenon occurs when DDS is used as the complex nitrogen source whether in the whole form or as the water soluble extract.

The most pertinent publications of which we are aware are as follows.

1. P. Rogovin, et al, 1970, "Continuous Fermentation to Produce Xanthan Biopolymers: Laboratory Investigation", *Biotechnol. Bioeng.*, XII, pp. 75-83.
2. K. W. Silman, et al., 1972, "Continuous Fermentation to Produce Xanthan Biopolymer: Effect of Dilution Rate", *Biotechnol. Bioeng.*, XIV, pp. 23-31.
3. P. Rogovin, U.S. Pat. No. 3,485,719, "Continuous Production of Xanthan".
4. G. P. Lindblom, et al., U.S. Pat. No. 3,328,262, "Heteropolysaccharide Fermentation Process".
5. Netherlands patent application No. 7,612,448, "Method for the Production of Bacterial Polysaccharides".
6. "Production of Polysaccharides by *Xanthomonas campestris* in Continuous Culture", FEMS Microbiology Letters, 347-349 (1978) by I. W. Davidson.
7. Process for the Production of Xanthan Gum, British patent application No. 2,008,138A (Tate and Lyle, LTD).

SUMMARY OF THE INVENTION

In producing xanthan gum in accordance with our invention, any species or strain of Xanthomonas organism may be employed in continuous culture in a nutrient medium, preferably under conditions of nutrient limited growth, when the medium is chemically defined and contains a defined organic supplement such as vitamins with or without certain amino acids (which may also constitute a defined nitrogen source) and in addition has present essential inorganic salts, glucose and $NH_4Cl$. Also, a chelating agent, as for example, citric acid, is employed to maintain solubility of iron and other trace elements present in the system.

The process of our invention can be either a single-stage or two-stage continuous fermentation procedure. Any conventional continuous stirred tank baffled reactor can be employed with provision for aseptic operation, agitation, aeration, temperature control, foam control, pH control, and measurement of dissolved oxygen tension. In carrying out our process, the medium is seeded with an inoculum of culture grown in the same medium as that used for the fermentation at an inoculum level of 5 to 10% of the medium volume. The culture is grown in batch mode for 24 to 48 hours until the desired cell concentration is reached-usually 1.5 to 2.5 grams of cells per liter. At that point, continuous flow of the medium is started into the fermenter such that the dilution rate is about 75% or less of the specific growth rate at which the organism is growing at that point. The medium is diluted continuously in the fermentor with a fermentable carbohydrate such as glucose. Continuous recovery of a volume of culture broth equal to the volume of medium introduced is also provided. Usually after two culture turnovers, the dilution rate is adjusted as desired. The process and microorganism may be regenerated after the rate of Xanthan production has been reduced substantially by the addition of citric acid. The concentration of citric acid in the medium after the addition should range from about 0.05 g/l to about 0.25 g/l. Preferably, the concentrate should be about 0.11 g/l.

Xanthan gum which is produced as a product of fermentation can be used without further purification, or filtered to remove cells, or can be precipitated with an alcohol such as ethyl or isopropyl alcohols with or without initial cell removal.

The following operating conditions may be employed:

| | |
|---|---|
| Dilution Rate: | 0.01–0.14 hr.$^{-1}$ |
| Preferred Range | 0.04–0.10 hr.$^{-1}$ |
| Temperature: | 20–35° C. |
| Preferred Range | 25–30° C. |
| pH: | 5.5–8.0 |
| Preferred Range | 6.4–7.4 |
| Air Rate: | 0.2–2 vol/vol-min |
| Preferred Range | 0.5–1 vol/vol-min |
| Agitation Rate: | 200–1200 rpm |
| Preferred Range | 500–800 rpm |

The expression "chemically defined medium" as used in the present description and claims is intended to mean one that contains in known composition and proportion essential mineral salts, trace elements, glucose or equivalent carbohydrate and defined supplemental organic growth factors; i.e., vitamins with or without appropriate amino acids such as L-histidine, L-methionine, and L-tryptophan. Other amino acids that may be included are glutamic acid, tyrosine, threonine, aspartic acid, asparagine, and arginine.

Representative species of the Xanthomonas genus which may be employed in carrying out our invention include *Xanthomonas carotae, Xanthomonas phaseoli, Xanthomonas papavericola, Xanthomonas begoniae, Xanthomonas hederae, Xanthomonas translucens, Xanthomonas vasculorum, Xanthomonas vesicatoria, Xanthomonas incanae,* and *Xanthomonas malvacearum.* Cultures of these organisms as well as others of this genus may be obtained from the American Type Culture Collection, Rockville, Md.

SPECIFIC EMBODIMENTS OF THE INVENTION

The process of our invention may be further illustrated by reference to the following specific examples, the first of which demonstrates that when dried distiller solubles (a complex undefined nitrogen source) is used in continuous culture, *Xanthomonas campestris* undergoes culture degeneration after seven to nine culture turnovers with subsequent loss of viscosity and xanthan productivity.

EXAMPLE I

*Xanthomonas campestris* strain B-1459 originally procured from the Northern Regional Research Center in Peoria, Ill., was maintained on YM agar slants at 4° C. and transferred to fresh agar slants at bi-weekly intervals.

For inoculum preparation, a loopful of culture from a fresh slant culture (<3 days old) was incubated into a 16×125 mm tube containing 7 ml of YM broth. The culture was incubated at 28° C., on a rotary shaker and 150 rmp, at a 20° inclination for 18 hours. At this point, the contents of the tube were transferred to 50 ml of YM broth (Difco) in a 500 ml Erlenmeyer flask, which was inoculated at 28° C. on a rotary shaker at 250 rpm for 18–24 hours. Next, the contents of the flask were transferred to 200 ml of YM broth contained in a 2000 ml Erlenmeyer flask. This was incubated under the same conditions as the 50 ml flask, for 18–24 hours.

This final volume was used to seed the fermenter at a ratio of 5% of the total volume of the medium in the fermenter. The culture was allowed to grow in a batch mode for 24–48 hours. Initial environmental conditions were as follows:

| | |
|---|---|
| Agitation | 300 rpm |
| Air Rate | 0.5 vol/vol/min |
| pH | 7.0 |
| Temperature | 28° C. |
| Dissolved Oxygen | 90% saturation |

After 15–18 hours, when viscosity and cell concentration increased to >500 cp and >1 gram/liter, respectively, the agitation was increased stepwise from 300 to 800 rpm and the air rate to 1 vol/vol/min.

When the cell concentration desired was reached (usually 1.8–2.5 gram/liter), the fermenter was switched to a continuous mode by pumping in fresh sterile medium at a desired flow rate and removing product at the same rate through an overflow level control device. The dilution rate (flow rate divided by fermenter medium volume) was initially set to be about 75% of the maximum specific growth rate of the culture. After two culture turnovers (a culture turnover is the time required to completely replace one volume of medium), the dilution rate was set to that desired in the range of 0.04–0.14 hr.$^{-1}$.

The medium employed in this example had the following composition:

| | |
|---|---|
| DDS Extract (10% sol'n) | 16 gm |
| K$_2$HPO$_4$ | 5 gm |
| MgSO$_4$ . 7H$_2$O | 0.2 gm |
| Glucose | 20.0 gm |
| Water | 1000 ml |

The results of this run are shown in the following table:

TABLE 1

| Time Period (Hrs) | Cell Conc'n (gm/l) | Xanthan Conc'n (%) | Viscosity (cp) | Xanthan Volumetric Productivity (gm/l/hr) | Xanthan Specific Productivity (gm/gm cells/hr) | Dilution Rate (hr$^{-1}$) | Total Culture Turnovers |
|---|---|---|---|---|---|---|---|
| 0 | | Start continuous culture | | | | | |
| 0–23 | 2.2–2.35 | .39–.45 | 100–240 | .33–.38 | .15–.16 | .085 | 0–2 |
| 23–68 | 2.5–2.8 | .58–.62 | 620–640 | .51–.53 | .18–.205 | .085 | 2–5.5 |
| 68–92 | 2.4–2.7 | .48–.51 | 680–720 | .43–.44 | .16–.175 | .088 | 5.5–7.5 |
| 92–119 | 1.4 | .33 | 160 | .26 | .18 | .078 | 7.5–10 |
| 119–162 | 2–2.5 | .11–.17 | <100 | .08–.13 | .04–.06 | .078 | 10–14 |

From the above data it is apparent that the B-1459 strain degenerates rapidly after 7.5 turnovers in the presence of DDS as evidenced by the sharp decrease in cell concentration and viscosity.

EXAMPLE II

This example shows that degeneration of *Xanthomonas campestris* NRRL B-1459 also occurs when it is grown in continuous culture on a mineral salts, glucose, $NH_4Cl$ medium. Procedural details employed in this example were the same as for Example I, except for the following changes:

During the inoculum preparation stage, the 7 ml YM culture was inoculated into 70 ml of YM broth in a 500 ml Erlenmeyer flask and incubated at 28° C., 250 rpm for 24 hours. This was then used to inoculate 700 ml of a mineral salts-glucose-ammonium chloride medium in a 2000 ml Fernbach flask. The minimal medium used in this last stage had the same composition as was used in the fermentation step as shown below:

TABLE II

| Component | Concentration (ppm) |
|---|---|
| Glucose | 22,000 |
| $NH_4Cl$ | 300 as N |
| KOH | 1000 + as K |
| $H_3PO_4$ | 150 as P |
| $MgSO_4$ | 40 as Mg |
| $CaCl_2$ | 10 as Ca |
| NaCl | 10 as Na |
| citric acid | 500 |
| $FeCl_3$ | 3 as Fe |
| $ZnSO_4$ | 1 as Zn |
| $CuSO_4$ | 0.6 as Cu |
| $MnSO_4$ | 0.3 as Mn |
| $Na_2MoO_4$ | 0.2 as Mo |
| $H_3BO_3$ | 0.1 as B |
| KI | 0.1 as I |

After the 700 ml culture was incubated at 28° C., 250 rpm for 40 hours, the entire culture was used to inoculate 20 liters of mineral salts, glucose-$NH_4Cl$ medium contained in a 28 liter New Brunswick fermenter (Model CMF-128S). Initial environmental conditions were as follows:

| | |
|---|---|
| Temperature | 28° C. |
| pH | 6.0 |
| Agitation | 230 rpm |
| Air Rate | 0.2–0.4 vol/vol/min |
| Dissolved $O_2$ | 90% saturation |

After an initial lag of about 30 hours, cell growth proceeded over the next 30 hours. When the cell concentration reached 0.9 gram per liter, continuous operation was started at a dilution rate of 0.07 hr.$^{-1}$. Within 48 hours, the cell concentration rose to 2.5 grams/liter. After about 10 culture turnovers, the viscosity and specific productivity started to decline and eventually was almost totally lost. The data for this run are summarized in the Table below and clearly demonstrate the inability of the B-1459 strain to produce xanthan in continuous fermentation using a minimal medium.

EXAMPLE III

In this Example the inoculation procedure was the same as outlined in Example I, as were the initial environmental conditions. The medium employed was a chemically defined medium having the following composition similar to Yeast Carbon Base (Difco).

TABLE IV

| Ingredient | Amt./Liter |
|---|---|
| Dextrose | 22.5 gm |
| L-Histidine-HCl | 1 mg |
| DL Methionine | 2 mg |
| L Tryptophan | 2 mg |
| Biotin | 2 mcg |
| Calcium Pantothenate | 400 mcg |
| Folic Acid | 2 mcg |
| Inositol | 2000 mcg |
| Niacin | 400 mcg |
| p-Aminobenzoic Acid | 200 mcg |
| Pyridoxine.HCl | 400 mcg |
| Riboflavin | 200 mcg |
| Thiamine.HCl | 400 mcg |
| Boric Acid | 500 mcg |
| Copper Sulfate | 40 mcg |
| Potassium Iodide | 100 mcg |
| Ferric Chloride | 3.98 mg |
| Manganese Sulfate | 400 mcg |
| Sodium Molybdate | 200 mcg |
| Zinc Sulfate | 400 mcg |
| Potassium Phosphate Monobasic | 1 gm |
| Magnesium Sulfate | 0.5 gm |
| Potassium Chloride | 0.57 gm |
| Sodium Chloride | 0.1 gm |
| Calcium Chloride | 0.1 gm |
| Ammonium Chloride | 1.53 gm |

The culture of *Xanthomonas campestris* B-1459 was grown under batch conditions for 40 hours at which time the cell concentration was 2.4 gm/liter. Continuous operation was then initiated at a dilution rate of 0.056 hr.$^{-1}$. There was a slight precipitate present in the medium upon makeup which was removed by sterile filtration. After approximately six turnovers the culture began to degenerate as indicated by a decrease in xanthan concentration and productivity. At this point the composition of the medium was changed by increasing the concentration of all components by 1.33 except for glucose, KCl, and $NH_4Cl$. Thereafter a sixfold concentrate of the medium was filtered through glass wool, which removed additional precipitate. Then the medium was diluted to final volume and subjected to sterile filtration. The result was a drastic decrease in cell concentration and almost complete loss of xanthan and viscosity. Thereafter citric acid was added to give a clear medium. It is to be understood that Applicant has found citric acid to be a useful chelating agent, but anticipates a number of commonly known chelating agents may be advantageously utilized in the present invention. The ultimate concentration of citric acid was 0.11 gm/l. Use of this revised medium resulted in a complete regain of prior cell concentration followed by

TABLE III

| Time Period (Hrs) | Cell Conc'n (gm/l) | Xanthan Conc'n (%) | Viscosity (cp) | Xanthan Volumetric Productivity (gm/l/hr) | Xanthan Specific Productivity (gm/gm cells/hr) | Dilution Rate (hr$^{-1}$) | Total Culture Turnovers |
|---|---|---|---|---|---|---|---|
| 0–34 | 1.3–1.9 | .26–.30 | 120–340 | .20 | .11–.15 | .07–.08 | 0–2.5 |
| 34–130 | 2.6–2.56 | .32–.39 | 640–850 | .23–.31 | .10–.13 | .07–.085 | 2.5–9.7 |
| 130–178 | 1.7–2.17 | .23–.265 | 420–430 | .17–.22 | .09–.10 | .07–.08 | 9.7–13.7 |
| 178–202 | 1.0 | .187 | 160 | .13 | .13 | .07 | 13.5–15 |
| 202–266 | .6–1.1 | .12–.14 | 28–78 | .1–.11 | .09–.175 | .077 | 15–20.1 | a recovery of xanthan productivity. Thereafter the culture was maintained for an additional 18 turnovers, which was approximately three times the number obtained in previous runs with dried distillers solubles. At the time the run was terminated, the culture was entirely normal. The results are shown in more detail in the following table:

TABLE V

| Time Period (Hrs) | Cell Conc'n (gm/l) | Xanthan Conc'n (%) | Viscosity (cp) | Xanthan Volumetric Productivity (gm/l/hr) | Xanthan Specific Productivity (gm/gm cells/hr) | Dilution Rate ($hr^{-1}$) | Total Culture Turnovers |
|---|---|---|---|---|---|---|---|
| 0–29 | 2.2–3.3 | .45–.71 | 1000–1950 | .25–.40 | .10–.13 | .056–.059 | 0–3 |
| 29–103 | 2.6–3.2 | .61–.75 | 1350–1980 | .32–.39 | .12–.13 | .043–.06 | 3–6.7 |
| 103–174 | 2.1–2.4 | .38–.50 | 450–1000 | .20–.30 | .09–.10 | .053–.061 | 6.7–9.3 |
| Degeneration occurring | | | | | | | |
| 174–205 | .3–.4 | .21–.30 | 100–250 | .10–.14 | .07–.09 | .046 | 9.3–10.9 |
| Reformulated medium with citric acid | | | | | | | |
| 205–239 | 2.6–3.05 | .28–.30 | 340–360 | .13–.15 | .05–.08 | .05 | 10.9–12.5 |
| 239–288 | 2.6–3.05 | .62–.68 | 800–1900 | .30–.33 | .10–.12 | .048 | 12.5–14.9 |
| 288–362 | 3.1–3.3 | .77–1.04 | 2000–3700 | .38–.46 | .12–.14 | .044–.05 | 14.9–18.9 |
| Increased dilution rate | | | | | | | |
| 362–411 | 2.5–3.0 | .77–1.04 | 200–280 | .26–.32 | .09–.13 | .10–.108 | 18.9–22.8 |
| Decreased dilution rate | | | | | | | |
| 411–504 | 2.7–3.2 | .35–.40 | 310–400 | .30–.36 | .11–.12 | .09 | 22.8–31 |

The above results demonstrate the ability of *Xanthomonas campestris* to produce xanthan gum from a relatively inexpensive chemically defined medium and the value of a chelating agent to solubilize iron and trace metal precipitates to reverse the cell degeneration process. The effect of dilution rate on xanthan gum concentration and viscosity is also illustrated.

EXAMPLE IV

Inoculum preparation was conducted in the same manner as in Example I as were the initial fermenter environmental conditions. Batch growth lasted 29 hours at the end of which time the cell concentration reached ~1.0 gram/liter. However, initial dilution rate was set too high at 0.08 hr.$^{-1}$ and the culture washed out over the next 40 hours, even after lowering the dilution rate to 0.05 hr.$^{-1}$. The culture was allowed to regrow in batch mode for 24 hours at which time the cell concentration reached 3.2 grams/liter. Continuous operation was started again at a dilution rate of 0.06 hr.$^{-1}$ and this time the culture lined out satisfactorily.

The culture was grown in batch mode and initially in continuous mode on Yeast Carbon Base medium (Difco) which composition is given below:

TABLE VI

| Component | Concentration (per liter) |
|---|---|
| $KH_2PO_4$ | 1.0 gm |
| $MgSO_4$ | 0.5 gm |
| NaCl | 0.1 gm |
| $CaCl_2$ | 0.1 gm |
| $H_3BO_3$ | 500 mcg |
| $CuSO_4$ | 40 mcg |
| KI | 100 mcg |
| $FeCl_3$ | 3.98 mg |
| $MnSO_4$ | 400 mcg |
| $Na_2MoO_4$ | 200 mcg |
| $ZnSO_4$ | 400 mcg |
| $NH_4Cl$ | 1.53 gm |
| L-Histidine | 1 mg |
| L-Methionine | 2 mg |
| L-Tryptophan | 2 mg |
| Glucose | 22.5 gm |
| Biotin | 2 mcg |
| Calcium Pantothenate | 400 mcg |
| Folic Acid | 2 mcg |
| Inositol | 2000 mcg |
| Niacin | 400 mcg |
| p-Aminobenzoic Acid | 200 mcg |
| Pyridoxine HCl | 400 mcg |
| Riboflavin | 200 mcg |
| Thiamine HCl | 400 mcg |
| Citric Acid | 167 mg |

Yeast Carbon Base medium is a chemically defined medium containing organic supplements in the form of vitamins with or without certain amino acids and does not contain yeast or other undefined nitrogen source. The term "Yeast Carbon Base" indicates that this medium was used originally to determine the carbon requirement of yeasts. After 146 hours of continuous operation, the medium was changed to Yeast Carbon Base at 1.5 times normal strength. After 240 hours of operation, 0.21% L-glutamic acid was added to the medium. Finally, after 453 hours of operations, the medium was replaced by one having the composition given in the table below.

TABLE VII

| Component | Concentration (per liter) |
|---|---|
| $KH_2PO_4$ | 0.88 gm |
| $K_2SO_4$ | 0.54 gm |
| $MgSO_4.7H_2O$ | 0.41 gm |
| $CaCl_2.2H_2O$ | 0.056 gm |
| Citric acid | 0.167 gm |
| $NH_4Cl$ | 1.53 gm |
| L-glutamic acid | 2.1 gm |
| Glucose | 22.5 gm |
| $FeCl_3$ | 10.1 mg |
| Trace Elements | Same as in Table II |

Pertinent operating data for this run are summarized below.

TABLE VIII

| Time Period (Hrs) | Cell Conc'n (gm/l) | Xanthan Conc'n (%) | Viscosity (cp) | Xanthan Volumetric Productivity (gm/l/hr) | Xanthan Specific Productivity (gm/gm cells/hr) | Dilution Rate ($hr^{-1}$) | Total Culture Turnovers |
|---|---|---|---|---|---|---|---|
| Yeast Carbon Base Medium | | | | | | | |
| 0–95 | 2.6–3.2 | .77–.83 | 2290–3670 | .41–.46 | .13–.17 | .054 | 0–4.9 |

TABLE VIII-continued

| Time Period (Hrs) | Cell Conc'n (gm/l) | Xanthan Conc'n (%) | Viscosity (cp) | Xanthan Volumetric Productivity (gm/l/hr) | Xanthan Specific Productivity (gm/gm cells/hr) | Dilution Rate (hr$^{-1}$) | Total Culture Turnovers |
|---|---|---|---|---|---|---|---|
| 95–146 | 2.0–2.8 | .24–.56 | 160–1170 | .25–.60 | .13–.22 | .102–.108 | 4.9–9.7 |
| | | Yeast Carbon Base at 1.5 Strength | | | | | |
| 146–240 | 2.1–2.3 | .26–.31 | 160–310 | .28–.33 | .138–.146 | .106–.108 | 9.7–17.3 |
| 240–263 | 2.7–3.2 | .36–.40 | 340–550 | .39–.41 | .12–.14 | .101–.109 | 17.3–20 |
| 263–352 | 4.1–4.7 | .67–.83 | 1680–2300 | .71–.87 | .168–.192 | .104–.106 | 20–29.7 |
| 352–453 | 3.9–4.8 | .65–.77 | 1690–2280 | .67–.83 | .153–.198 | .102–.108 | 29.7–41.7 |
| 453–501 | 3.2–3.5 | .62–.68 | 1160–1840 | .63–.71 | .185–.206 | .102–.105 | 41.7–46 |

In this case the vitamins were removed and glutamic acid was included to provide 10% of the total carbon (90% from glucose) and 33% of the total nitrogen.

Examples III and IV show that when a Xanthomonas organism is used to ferment a chemically defined medium, the process lends itself well to continuous fermentation conditions to produce xanthan gum of good quality. The process described above, while a single-stage method, can also be operated as a two-stage procedure using any medium coming within the scope of that defined herein. In a two-stage process, cell production and xanthan production would both occur in the first stage, while xanthan production primarily would occur in the second stage since the cell growth limiting nutrient would be exhausted from the medium.

We claim:

1. A continuous process for the production of a heteropolysaccharide which comprises continuously culturing a microorganism of the genus Xanthomonas in a liquid chemically defined medium free of yeast or other undefined nitrogen source, but containing both a chelating agent and organic supplements in the form of water soluble growth factors which permits said organism to grow and produce said heteropolysaccharide in a stable non-degenerative state and wherein the growth limiting nutrient in said medium is any of the nutrients normally used in said process, culturing said microorganism in said medium without discontinuing the fermentation process and withdrawing heteropolysaccharide from said medium at a rate such that an essentially steady state condition is maintained.

2. A process for the production of a heteropolysaccharide by means of continuous fermentation which comprises cultivating a microorganism of the genus Xanthomonas in a chemically defined medium free of yeast or other undefined nitrogen source, but containing both a chelating agent and organic supplements in the form of water soluble growth factors which permits said organism to grow and produce said heteropolysaccharide in a stable non-degenerative state and wherein the growth limiting nutrient is any of the nutrients normally used in said process so that production of said microorganism is maximized, thereafter continuously feeding the resulting broth containing the microorganisms thus produced in said medium to a second stage into which a fermentable carbohydrate is continuously fed and withdrawing heteropolysaccharide from said medium at a rate such that an essentially steady state condition is maintained, whereby the formation of heteropolysaccharide in said second stage is maximized.

3. The process of claim 1 or 2 in which the medium employed is Yeast Carbon Base medium.

4. The process of claim 1 or 2 in which the medium employed is a glucose-mineral salts medium containing an amino acid having assimilable nitrogen.

5. The process of claim 4 in which the medium employed contains L-glutamic acid.

6. The process of claim 1 or 2 in which the growth limiting nutrient is nitrogen.

7. The process of claim 1 or 2 in which the microorganism employed is *Xanthomonas juglandis*.

8. The process of claim 1 or 2 in which the microorganism employed is *Xanthomonas campestris*.

9. The process of claim 1 or 2 in which the microorganism employed is *Xanthomonas vesicatoria*.

10. The process of claim 1 or 2 in which the heteropolysaccharide is Xanthan.

11. The process of claim 2 wherein said resulting broth is diluted at a rate of less than 75% of the specific growth rate at which said microorganism is growing.

12. The process of claim 1 or 2 wherein after the rate of production of heteropolysaccharides is substantially reduced, the process additionally comprises adding citric acid.

13. The process of claim 12 wherein said citric acid in said medium has a concentration ranging from 0.05 g/l to 0.25 g/l.

14. The process of claims 1 or 2 wherein the organic supplement is comprised of at least one member selected from the group consisting of vitamins and amino acids.

15. The process of claims 1 or 2 wherein the cheating agent is citric acid.

* * * * *